United States Patent [19]

Ono et al.

[11] Patent Number: 4,954,125
[45] Date of Patent: Sep. 4, 1990

[54] CATALYST FOR POLYMERIZATION OF CONJUGATED DIENE AND PROCESS FOR PRODUCING CONJUGATED DIENE POLYMER

[75] Inventors: Hisao Ono; Ryuji Sato; Takumi Miyachi, all of Yokkaichi, Japan

[73] Assignee: Japan Synthetic Rubber Company, Ltd., Tokyo, Japan

[21] Appl. No.: 208,664

[22] Filed: Jun. 20, 1988

[30] Foreign Application Priority Data

Jul. 20, 1987 [JP]  Japan .................................. 62-180605

[51] Int. Cl.$^5$ ........................ C08F 4/609; C08F 36/06
[52] U.S. Cl. ..................................... 526/138; 502/117; 526/139; 526/335; 568/13; 585/369; 585/508
[58] Field of Search ........................ 526/92, 138, 139

[56] References Cited

U.S. PATENT DOCUMENTS

| | | | |
|---|---|---|---|
| 3,498,963 | 3/1970 | Ichikawa et al. ................... | 526/138 |
| 3,522,332 | 7/1970 | Ichikawa et al. ................... | 526/139 |
| 4,182,813 | 1/1980 | Makino et al. ...................... | 526/139 |
| 4,306,085 | 12/1981 | Kim et al. . | |

FOREIGN PATENT DOCUMENTS

| | | |
|---|---|---|
| 155551 | 9/1985 | European Pat. Off. . |
| 2392080 | 12/1978 | France . |
| 1158296 | 7/1969 | United Kingdom . |

OTHER PUBLICATIONS

J. Org. Chem., vol. 25, Nov. 1960, pp. 2001–2006, A. E. Senear et al., "Derivatives of Triphenylphosphine and Triphenylphosphine Oxide".

J. Liebigs Annalen Der Chemie, vol. 715, 1968, pp. 1–14, H. Goetz et al., "Experimentelle Befunde zur Ladungsverteilung in Atylphosphin-[p-nitro-phenyl]".

Primary Examiner—Edward J. Smith
Attorney, Agent, or Firm—Oblon, Spivak, McClelland, Maier & Neustadt

[57] ABSTRACT

A catalyst consisting essentially of (A) a cobalt compound and (B) an organic phosphorus compound represented by the formula:

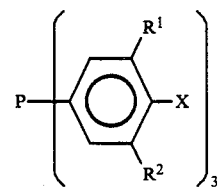

wherein $R^1$ and $R^2$ are independently hydrogen atoms, alkyl groups or aryl groups, and three X's, which may be the same or different, are electron-donating groups. This catalyst is effectively used in a process for producing a conjugated diene polymer by polymerizing a conjugated diene in a hydrocarbon or halogenated hydrocarbon solvent in the presence of the above catalyst together with (C) an organoaluminum compound and (D) 0.25–1.5 mols, per mol of the organoaluminum compound (C), of water.

15 Claims, 4 Drawing Sheets

CATALYST FOR POLYMERIZATION OF CONJUGATED DIENE AND PROCESS FOR PRODUCING CONJUGATED DIENE POLYMER

This invention relates to a catalyst for polymerizing a conjugated diene, a novel compound used as one of the essential components of the catalyst, and a process for producing a crystalline conjugated diene polymer using the catalyst.

Several types of catalysts have heretofore been known for the production of a crystalline 1,2-polybutadiene. U.S. Pat. No. 3,498,963, for example, discloses a process for producing a syndiotactic 1,2-polybutadiene using a catalyst composed of a cobalt compound, an organoaluminum compound, water and an organic phosphorus compound which is a phosphine or phosphite compound, or using a catalyst composed of a cobalt compound-organic phosphorus compound complex, an organoaluminum compound and water.

Further, U.S. Pat. No. 4,182,813 discloses a process for producing a syndiotactic 1,2-polybutadiene having a high crystallinity using a cobalt compound, an organoaluminum compound, water and an organic phosphorus compound represented by the following general formula, which is a derivative of triphenylphosphine:

wherein $R^3$ is an alkyl group or an aryl group, each of $R^4$ and $R^5$ is hydrogen or an alkyl or aryl group. It has also been proposed that a 1,2-polybutadiene having a high crystallinity can be produced by carrying out the polymerization at a low temperature.

However, when a 1,2-polybutadiene having a high crystallinity is produced at a low polymerization temperature according to the above proposal, the catalyst activity during the polymerization is low and the productivity becomes low. When the amount of catalyst used is increased in order to enhance the productivity, the thermal stability of the polymer formed becomes inferior, and a larger amount of the cobalt compound remains in the polymer, which results in deterioration of color of the polymer.

Generally, it has been considered that in the polymerization reaction for obtaining a polymer having a high stereoregularity, the catalyst activity is low and accordingly the productivity is low.

The present inventors have found that the use of a novel organic phosphine compound as a ligand for catalyst can provide a polymer having an improved stereoregularity, an improved crystallinity and an improved polymerization activity. Consequently, the problems which the conventional processes could not solved have been solved.

An object of this invention is to provide a catalyst having a high polymerization activity for polymerizing a conjugated diene.

Another object of this invention is to provide a novel organic phosphorus compound which is useful as a ligand for the above catalyst.

A further object of this invention is to provide a process for producing a conjugated diene polymer having an improved crystallinity which comprises polymerizing a conjugated diene with the above catalyst.

The other objects and advantages of this invention will become apparent from the following description and the accompanying drawings. In the accompanying drawings.

According to this invention, there is provided a catalyst composed essentially of (A) a cobalt compound and (B) an organic phosphorus compound represented by the formula:

wherein $R^1$ and $R^2$ are independently hydrogen atoms, alkyl groups or aryl groups and X's, which may be the same or different, are electron-donating groups.

This invention further provides an organic phosphorus compound represented by the formula:

wherein $R^1$ and $R^2$ are independently hydrogen atoms, alkyl groups or aryl groups and X's, which may be the same or different, are electron-donating groups, and a process for producing said organic phosphorus compound.

This invention furthermore provides a process for producing a conjugated diene polymer which comprises polymerizing a conjugated diene in a hydrocarbon or halogenated hydrocarbon solvent in the presence of (A) a cobalt compound, (B) an organic phosphorus compound, (C) an organoaluminum compound and (D) 0.25–1.5 mols, per mol of the organoaluminum compound (C), of water, characterized in that the compound (B) is an organic phosphorus compound represented by the formula:

wherein $R^1$ and $R^2$ are independently hydrogen atoms, alkyl groups or aryl groups and X's, which may be the same or different, are electron-donating groups.

The cobalt compound which is the component (A) of this invention is a compound of mono-, di- or trivalent cobalt and includes, for example, cobalt halides such as cobalt chloride, cobalt bromide, cobalt iodide and the like; cobalt salts of organic or inorganic acids such as cobalt sulfate, cobalt nitrate, cobalt carbonate, cobalt phosphate, cobalt naphthenate, cobalt octenoate and the like; cobalt hydroxide; cobalt cyanide; cobalt thiocyanide; and cobalt complexes having, as a ligand, carbonyl, isonitrile, a vinyl compound, cyclopentadienyl, $\pi$-allyl, a derivative of one of them, acetylacetone, acetoacetic acid or the like. Preferable examples are cobalt(II)-triphenylphosphine complex, cobalt(II) acetylacetonate, cobalt octenoate, cobalt naphthenate, cobalt(II) chloride, cobalt(II) bromide, cobalt(II) iodide, pyridine complexes of these cobalt halides, cobalt ethylxanthogenate and the like. More preferable cobalt compounds are cobalt chloride, cobalt bromide, cobalt iodide, cobalt octenoate and cobalt naphthenate.

The component (B) is a novel organic phosphorus compound represented by the general formula:

wherein $R^1$ and $R^2$ are independently hydrogen atoms, alkyl groups or aryl groups and X's, which may be the same or different, are electron-donating groups. $R^1$ and $R^2$ are preferably alkyl groups, the number of carbon atoms of which is not critical but preferably 1–4, more preferably 1 or 2, most preferably 1. Preferably, at least one of $R^1$ and $R^2$ is an alkyl group, and more preferably, both of them are alkyl groups.

Each X is preferably a group represented by the general formula, $-O-R^6$ or

In the formula, $R^6$ is hydrogen or an alkyl group, preferably an alkyl group. The alkyl group has preferably 1–6, more preferably 1–4, most preferably 1–2 carbon atoms. $R^7$ and $R^8$ are independently selected from the group consisting of hydrogen, an alkyl group and a phenyl group. Preferably, at least one of $R^7$ and $R^8$ is an alkyl group. The alkyl group has preferably 1–6, more preferably 1–4, most preferably 1–2 carbon atoms.

Specific examples of X are a methoxy group, an ethoxy group, a butoxy group, a phenoxy group, a hydroxyl group, a dimethylamino group, a diethylamino group, a dipropylamino group, a dibutylamino group, a methylamino group, an ethylamino group and an amino group. The methoxy group and the ethoxy group are preferred, and the methoxy group is more preferable.

Specific examples of the organic phosphorus compound (B) are tris(4-methoxyphenyl)phosphine, tris(3-methyl-4-methoxyphenyl)phosphine, tris(3,5dimethyl-4-methoxyphenyl)phosphine, tris(3-ethyl-4-methoxyphenyl)phosphine, -tris(3,5-diethyl-4-methoxyphenyl)phosphine, tris(3,5-diisopropyl-4-methoxyphenyl)phosphine, tris(3,5-di-t-butyl-4-methoxyphenyl)phosphine and tris(3,5-dimethyl-4-dimethylaminophenyl)phosphine. Of these, tris(3,5-dimethyl-4-methoxyphenyl)phosphine is most preferable.

The organic phosphorus compound (B) can be prepared according to any method. However, it is preferable to use, as the starting material, a 2,6-dialkylphenol such as 2,6-dimethylphenol or the like.

For instance, the objective phosphine compound can be produced by reacting 2,6-dimethylphenol with a halogen such as chlorine, bromine or the like into a 4-halo-2,6-dimethylphenol; dissolving the halogenation product in an aqueous alkali solution, then alkylating it with an alkylating agent such as a dialkyl sulfate (the alkyl is methyl or ethyl) or the like; reacting the alkylation product with magnesium to prepare a Grignard reagent; and reacting the Grignard reagent with a phosphorus trihalide, a trialkyl phosphite or a triaryl phosphite.

The organic phosphorus compound (B) of this invention, a representative of which is a tris(3,5-dimethyl-4-alkoxyphenyl)phosphine, can be used as a catalyst for polymerizing a conjugated diene and also as a ligand for transition metal. Its complex with nickel dicarbonyl, represented by the general formula $Y_2Ni(CO)_2$ [Y is the organic phosphorus compound (B) of this invention] can be used in the Reppe reaction to conduct the dimerization or trimerization of acetylene, butadiene or the like. The organic phosphorus compound (B) can also form a complex of $Y_4Ni$ type, a complex of $Y_4Pd$ type, a complex of $Y_2PdCl_2$ type and a complex of $Y_3Pt$ type, and these complexes can be used as a catalyst for dimerization of butadiene, a catalyst for synthesis of isocyanate by oxidizing isonitrile, a catalyst for formation of a carboxylic acid from an unsaturated olefin, and a catalyst for formation of an allyl ester from allyl alcohol and carbon monoxide.

Further, the organic phosphorus compound (B) can be reacted with a halogen such as bromine or the like to obtain a phospholan compound which is a halogenation reagent.

Furthermore, the organic phosphorus compound (B) can be substituted for the triphenylphosphine used in organic synthesis reactions.

In this invention, when for the organic phosphorus compound (B) is substituted a triphenylphosphine derivative which has an electron-donating substituent (e.g. methoxy) at the ortho-position to phosphorus on the benzene ring, it is impossible to obtain a conjugated diene polymer having a high crystallinity. The effect of this invention can be obtained only when as the organic phosphorus compound (B) is used a triphenylphosphine compound having an electron-donating group at the para-position to phosphorus on the benzene ring.

In the catalyst of this invention, the cobalt compound (A) and the organic phosphorus compound (B) may form a complex in advance. When the catalyst is a complex of the cobalt compound (A) with the organic phosphorus compound (B), it is not necessary to use the organic phosphorus compound (B) additionally.

The organoaluminum compound which is the component (C) used in polymerization is at least one member selected from the group consisting of compounds represented by the formulas, $AlR_3$ (R is an alkyl group)

and AlR$_2$Y (R is an alkyl group and Y is a halogen such as chlorine, bromine, iodine or the like). The alkyl group can be a straight chain or a branched chain and preferably has 1-6 carbon atoms. Preferable examples of the organoaluminum compound (C) are triethylaluminum, tripropylaluminum, triisopropylaluminum, tributylaluminum, triisobutylaluminum, trihexylaluminum, triphenylaluminum, diethylaluminum monochloride, dipropylaluminum · monochloride, diisobutylaluminum monochloride and the like. More preferable are triethylaluminum, tributylaluminum, a mixture of triethylaluminum and diethylaluminum monochloride and a mixture of triisobutylaluminum and diethylaluminum monochloride.

The conjugated diene which can be polymerized according to the process of this invention is butadiene, isoprene or piperylene. Of these, butadiene is most preferable.

The catalyst of this invention can be prepared according to any method; however, the catalyst preparation is preferably conducted in a hydrocarbon or halogenated hydrocarbon solvent. The individual components for the catalyst may be previously mixed before they are contacted with a conjugated diene to be polymerized. However, it is preferable that the catalyst components be mixed in a polymerization reactor in the presence of a conjugated diene.

The temperature at which the catalyst preparation is effected is not critical but is ordinarily −20° to 50° C.

In the catalyst of this invention, the proportion of the organoaluminum compound (C) to the cobalt compound (A) is preferably 1-1,000 mols, more preferably 5-100 mols, of the organoaluminum compound (C) per mole of the cobalt compound (A). Since the proportion does not largely affect the vinyl content and crystallinity of the polymer formed, the proportion can be selected depending upon the polymerization activity desired and the molecular weight required for the polymer to be formed.

The amount of water, the component (D), used in polymerization has a close connection with the amount of the organoaluminum compound (C) used and is 0.25-1.5 mols per mole of the organoaluminum compound (C). When the amount of water used is less than 0.25 mol or more than 1.5 mols per mole of the organoaluminum compound (C), the polymerization activity is greatly low. The amount of water used is preferably 0.5-1 mol per mol of the organoaluminum compound (C). The amount of water used referred to herein implies the total amount of water present in the polymerization system.

The amount of the organic phosphorus compound (B) used is preferably 0.5 mol or more, more preferably 0.5-10 mols, most preferably 1-5 mols, per mol of the cobalt compound (A). When the amount of the organic phosphorus compound (B) used is less than 0.5 mol, it is difficult to obtain a conjugated diene polymer having a high 1,2-content.

The polymerization reaction can be conducted continuously or batchwise by contacting a conjugated diene with the catalyst of this invention in a hydrocarbon or halogenated hydrocarbon solvent.

The amount of the catalyst used in the polymerization reaction is preferably about 0.001-1 mmol, more preferably about 0.01-0.5 mmol as the cobalt compound (A), per mol of the conjugated diene to be polymerized.

The polymerization temperature is preferably −50° to 100° C., more preferably −20° to 80° C. The crystallinity of the conjugated diene polymer formed varies depending upon the polymerization temperature, and the lower the polymerization temperature, the higher the crystallinity of the polymer formed. Therefore, the polymerization temperature can be appropriately selected depending upon the organic phosphorus compound (B) used and the desired crystallinity.

The pressure used in the polymerization reaction is not critical and may be any pressure as long as it can allow the reaction mixture to stay in a substantially liquid phase.

The hydrocarbon or halogenated hydrocarbon solvent used in the polymerization reaction or in the catalyst preparation includes aliphatic hydrocarbons such as npentane, n-hexane, n-heptane, isooctane and the like; alicyclic hydrocarbons such as cyclohexane, decalin, tetralin and the like; aromatic hydrocarbons such as benzene, toluene, xylene, cumene and the like; and halogenated hydrocarbons such as methylene chloride, chloroform, carbon tetrachloride, trichloroethylene, perchloroethylene, chlorobenzene, bromobenzene, chlorotoluene and the like. Of these, the halogenated hydrocarbons are preferred and methylene chloride is especially preferred.

When the polymerization reaction has proceeded to a desired stage, there are added to the reaction mixture a polymerization terminator (e.g. an alcohol or the like), an age resister, an anti-oxidant, an ultraviolet absorber, etc. Then, the polymer formed is separated, washed and dried in the conventional manner to obtain a desired conjugated diene polymer.

According to the process of this invention, even under the same polymerization conditions as in the conventional methods, a conjugated diene polymer having a crystallinity which has been desirably controlled in a range of usually 5% to about 50%, preferably 10% to about 50% canbe produced in a high yield by selecting the specific organic phosphorus compound and/or polymerization temperature. In addition, in the present process, the handling of the polymerization mixture is easy, and a 1,2- polybutadiene having a crystallinity of 25-50%, preferably 25-40% whose production has heretofore been difficult can be produced easily in a high yield at a polymerization temperature of about −30° to 30° C. (which is desirable in industrial practice) without requiring any particular lower temperature. As compared with the use of, for example, triphenylphosphine, the use of the specific organic phosphorus compound of this invention can advantageously give a 1,2-polybutadiene whose crystallinity is about 7-15% higher, under the same polymerization conditions.

The polymer obtained according to the present process is superior in transparency, processability, strength, elastic modulus, etc. The polymer has a vinyl content of 80% or more, preferably 90% or more, more preferably 93% or more.

According to this invention, a conjugated diene polymer having a high crystallinity can be obtained in a high yield. The conjugated diene polymer has a high crystallinity and a high melting point, and hence, its heat resistance is superior. Further, since the polymer is produced in a high yield, the productivity is high. Furthermore, the amount of cobalt remaining in the polymer formed is small, and accordingly, the polymer has excellent heat-aging resistance.

Moreover, the cobalt complexes containing the organic phosphorus compound of this invention as a ligand can be used as a highly active catalyst for 1,2-polybutadiene.

The conjugated diene polymer obtained according to the present process can be used alone or in combination with rubbers and/or resins, in many applications. Typical applications include various molded articles (e.g. stretched film, shrinkable film, laminate film, various tubes and hoses, heat-fusible adhesive, footwear), materials for photosensitive resins, etc.

This invention is explained more specifically below referring to Examples However, this invention should not be construed to be restricted to these Examples In the following Examples and Comparative Examples, the microstructure of each polymer obtained was calculated according to the Morero method, using the infrared absorption spectrum.

The crystallinity of each polymer was measured according to the gradient density tube method by setting the density of a 1,2-polybutadiene having a crystallinity of 0% at 0.8920 g/cm$^3$ and the density of a 1,2-polybutadiene having a crystallinity of 100% at 0.9600 g/cm$^3$.

The intrinsic viscosity [η] of each polymer was measured at 30° C. in toluene as a solvent.

EXAMPLE 1

[Preparation of catalyst]

2.15 g (88.4 mmols) of magnesium was placed in a 300-ml glass container and thoroughly dried by heating. Thereto were added 5 ml of tetrahydrofuran (THF) and several drops of 4-bromo-2,6-dimethylanisole, and the mixture was heated slightly to cause Grignard reaction When the reaction started, 45 ml of THF was further added and a solution of 19.0 g (88.3 mmols) of 4-bromo-2,6-dimethylanisole in 50 ml of THF was added dropwise at such a rate that THF was mildly refluxed After the completion of the dropwise addition and when the heat generation stopped and substantially all the magnesium was consumed, a solution of 8.52 g (27.5 mmols) of triphenyl phosphite in 30 ml of THF was added dropwise. After the completion of the dropwise addition, the reaction mixture was heated under reflux for 1 hour to complete the reaction The reaction mixture was hydrolyzed and extracted with toluene. The extract was subjected to evaporation to obtain a white powder. The powder was recrystallized from ethanol to obtain 9.33 g (21.4 mmols, 78%) of tris(4- methoxy-3,5-dimethylphenyl)phosphine as a white powder. The phosphine had a melting point of 176° C. as measured by a differential scanning colorimeter.

Figure 1:
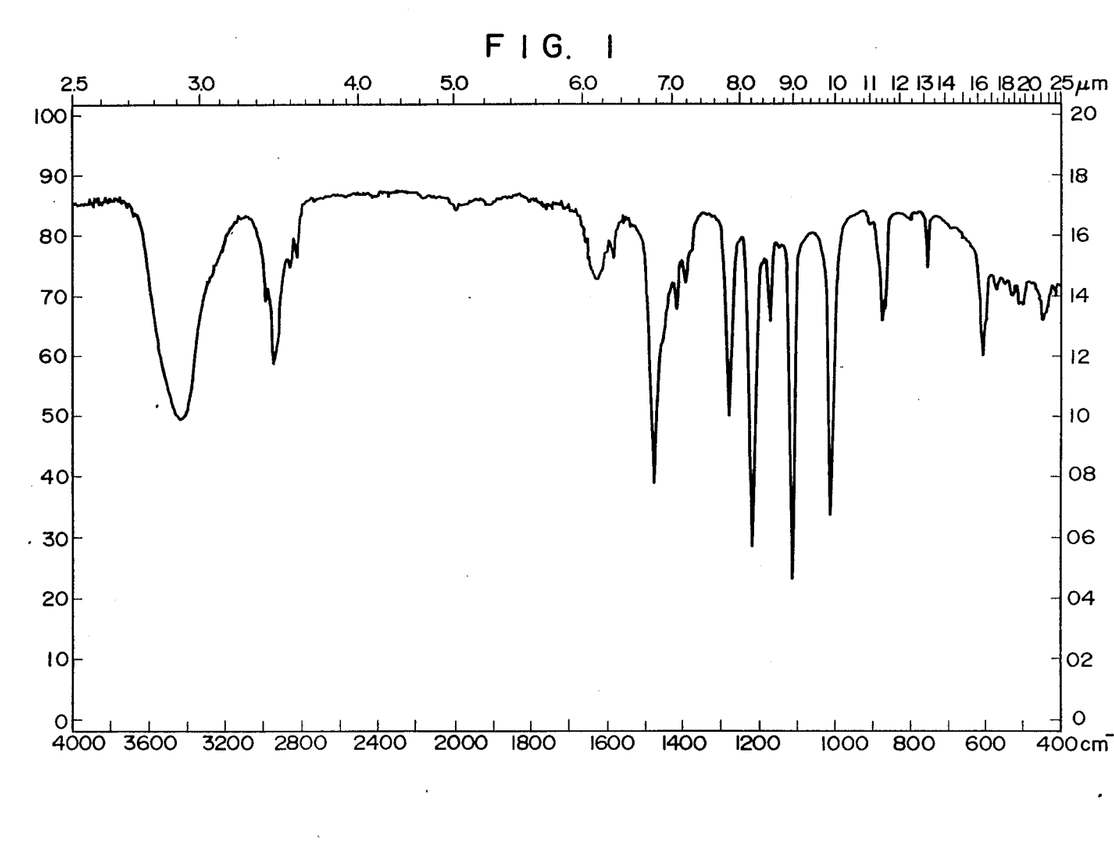
FIGS. 1 and 2 are the infrared absorption spectra of the phosphine compounds obtained in Examples 1 and 7, respectively.
Figure 3:
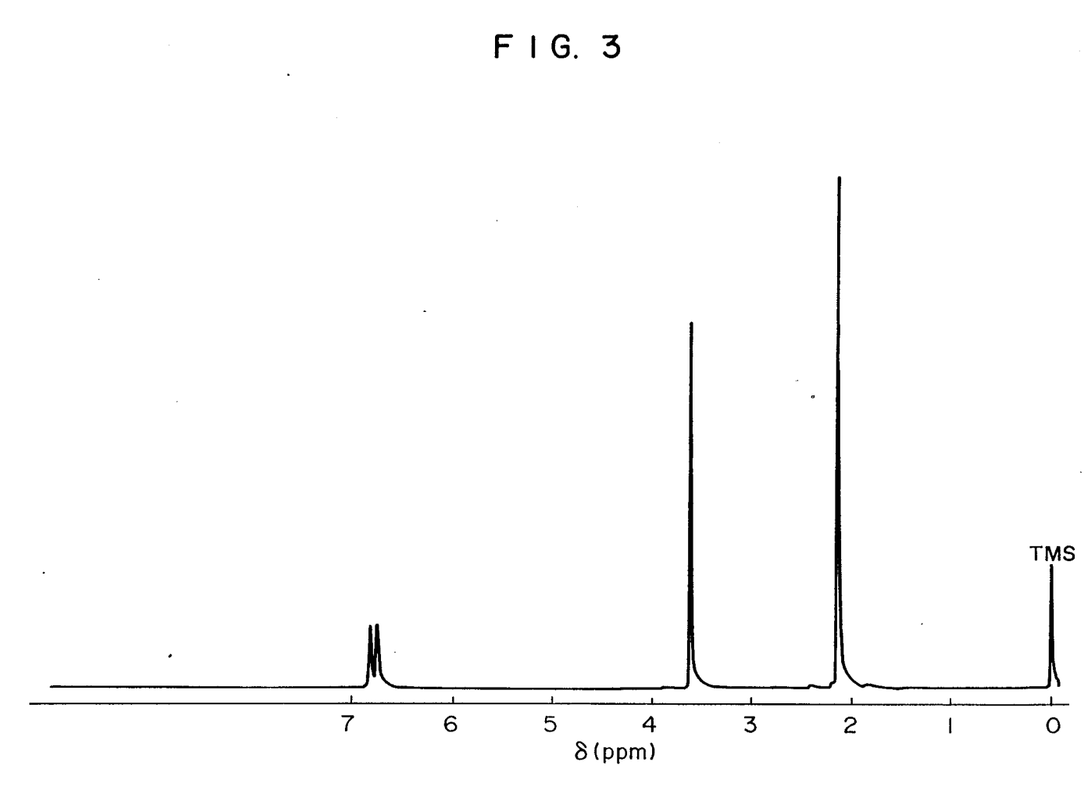
FIGS. 3 and 4 are the NMR spectra of the phosphine compounds obtained in Examples 1 and 7, respectively.

The elemental analysis, infrared absorption spectrum (KBr method) and $^1$H-NMR spectrum (solvent: carbon disulfide) of the above phosphine are shown in Table 1, FIG. 1 and FIG. 3, respectively.

In a 100-ml graduated flask were placed a rotor, 0.48 g (2.2 mmols) of anhydrous cobalt chloride and 1.744 g (4 mmols) of the tris(3,5-dimethyl-4-methoxyphenyl)-phosphine produced above. The flask was purged with nitrogen. Thereto was added methylene chloride which had been subjected to a drying treatment, to make the total amount 100 ml.

The flask was placed in a water bath at 40° C. and the flask contents were stirred for 10 hours. Then, the flask was allowed to stand for 24 hours at room temperature. The cobalt concentration in the supernatant liquid was measured to find to be 0.0196 mol/liter.

The thus prepared mixture of cobalt bromide and tris(3,5-dimethyl-4-methoxyphenyl)phosphine was used as a catalyst in the following polymerization. [The mixture is hereinafter referred to as the cobalt-phosphine solution (A).]

[Polymerization]

A 1-liter separable flask equipped with a stirrer, a thermometer and a nitrogen-feeding device was evacuated. The separable flask was heated by means of a gas burner to dry its inside and then cooled. Purging with nitrogen was repeated three times. Then, in the flask were placed 530 g (400 ml) of methylene chloride which had been subjected to a nitrogen bubbling treatment, 42 g of butadiene and 0.4 mmol (7.2 mg) of water. To the resulting mixture were added 4.0 ml (0.8 mmol as triisobutylaluminum) of a 0.2 mol/liter solution of triisobutylaluminum in methylene chloride and 3.67 ml (0.072 mmol as cobalt atom) of the cobalt-phosphine solution (A) with stirring at −5° C., to start polymerization.

The polymerization was effected for 1 hour while the temperature was kept at −5° C. A small amount of water was added to stop the polymerization. Methanol containing an age resister was added to the polymerization mixture to coagulate the polymer formed. The coagulation product was dried at 60° C. for 14 hours in a vacuum drier, and the drying was stopped when the polymer weight became constant.

The polymer obtained was measured for physical properties. The results are shown in Table 2.

EXAMPLES 2 and 3

Using the cobalt-phosphine solution (A) prepared in Example 1, polymerization was conducted by repeating the same procedure as in Example 1, except that the polymerization temperature was changed to 0° C. or 10° C. The polymers obtained were evaluated, and the results are shown in Table 2.

COMPARATIVE EXAMPLE 1

[Preparation of catalyst]

A cobalt-phosphine solution (B) (cobalt concentration: 0.0196 mol/liter) was prepared by repeating the same procedure as in Example 1, except that tris(3,5-xylyl)phosphine was substituted for the tris(3,5-dimethyl-4methoxyphenyl)phosphine used in Example 1.

[Polymerization]

Polymerization was conducted by repeating the same procedure as in Example 1, except that the above solution (B) was substituted for the cobalt-phosphine solution (A) used in Example 1.

The polymer obtained was evaluated. The results are shown in Table 2.

COMPARATIVE EXAMPLE 2

[Preparation of catalyst]

A cobalt-phosphine solution (C) (cobalt concentration: 0.0198 mol/liter) was prepared by repeating the same procedure as in Example 1, except that triphenylphosphine was substituted for the tris(3,5-dimethyl-4-methoxyphenyl)phosphine used in Example 1.

[Polymerization]

Polymerization was conducted by repeating the same procedure as in Example 1, except that the above solution (C) was substituted for the cobalt-phosphine solution (A) used in Example 1.

The polymer obtained was evaluated, and the results are shown in Table 2.

Example 4

Polymerization was conducted by repeating the same procedure as in Example 1, except that 3.6 ml (0.072 mmol as cobalt atom) of a methylene chloride solution of a complex of cobalt bromide and tris(3,5-dimethyl-4methoxyphenyl)phosphine [structural formula of the complex:

$$CoBr_2[P(\text{―}C_6H_2(CH_3)_2\text{―}OCH_3)_3]_2]$$

(the cobalt concentration in the solution: 0.02 mol/liter) [the solution is hereinafter referred to as the cobalt-phosphine complex solution (A)] was substituted for the cobalt-phosphine solution (A) used in Example 1.

The polymer obtained was evaluated, and the results are shown in Table 2.

COMPARATIVE EXAMPLE 3

[Preparation of catalyst]

A cobalt-phosphine solution (D) (cobalt concentration: 0.0195 mol/liter) was prepared by repeating the same procedure as in Example 1, except that tris(2,6-dimethoxyphenyl)phosphine was substituted for the tris(3,5-dimethyl-4-methoxyphenyl)phosphine used in Example 1.

[Polymerization]

Polymerization was conducted by repeating the same procedure as in Example 1, except that the above solution (D) was substituted for the cobalt-phosphine solution (A) of Example 1.

However, substantially no polymer was produced.

COMPARATIVE EXAMPLE 4

Polymerization was conducted by repeating the same procedure as in Example 4, except that a cobalt bromidebis(triphenylphosphine) complex was substituted for the complex of cobalt bromide and tris(3,5-dimethyl-4methoxyphenyl)phosphine used in Example 4. The results are shown in Table 2.

COMPARATIVE EXAMPLE 5

Polymerization was conducted by repeating the same procedure as in Example 1, except that the molar ratio of $H_2O/Al$ was changed to 2. However, no polymer was produced

EXAMPLES 5 and 6

The same procedure as in Example 1 was repeated, except that the kind of the organic phosphorus compound was changed. The results obtained are shown in Table 2.

EXAMPLE 7

[Preparation of phosphine compound]

A white crystal of tris(4-ethoxy-3,5dimethylphenyl)phosphine having a melting point of 122° C. was obtained in a yield of 75% by repeating the same procedure as in Example 1, except that 1-bromo-4-ethoxy3,5-dimethylbenzene was substituted for the 4-bromo-2,6-dimethylanisole used in Example 1.

Figure 2:
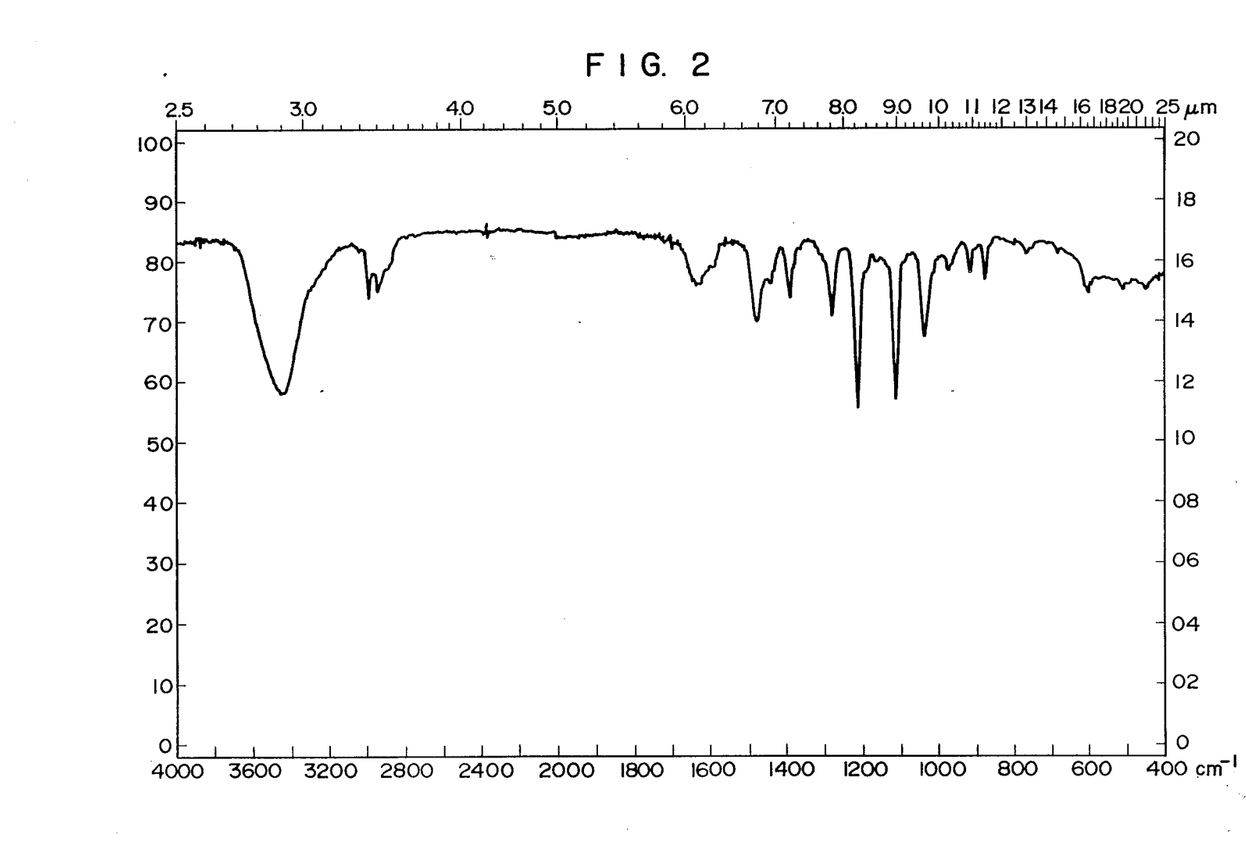
Figure 4:
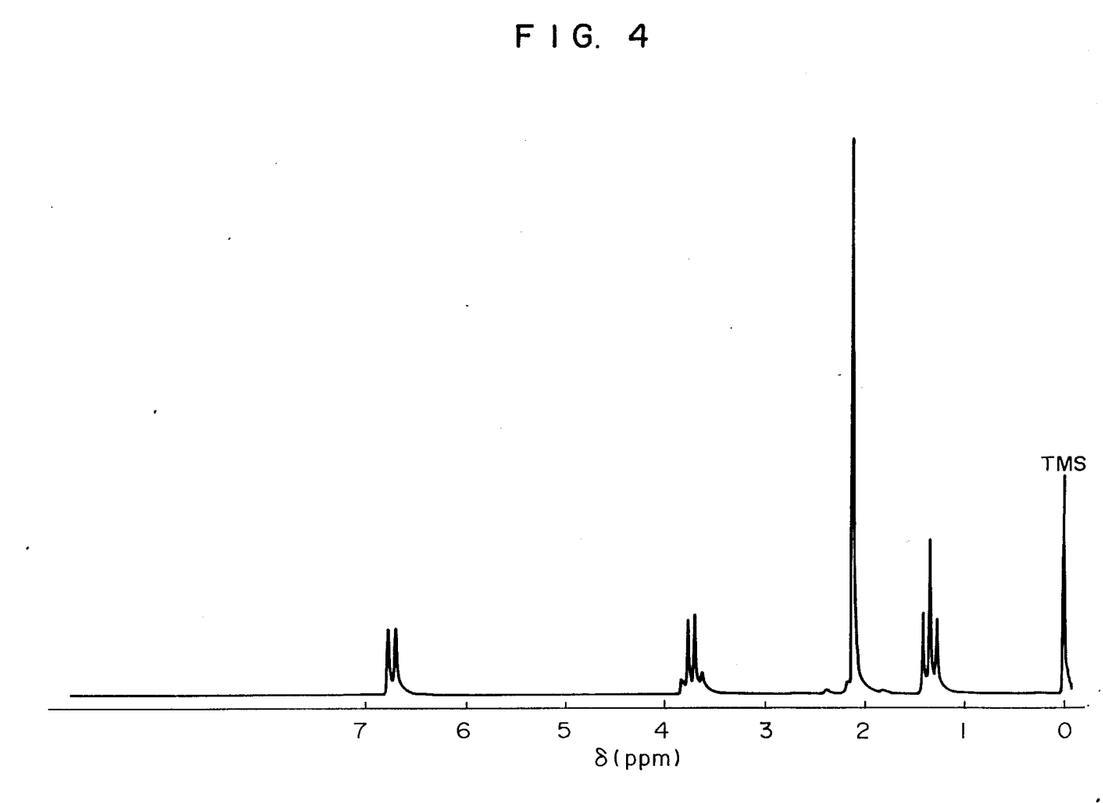

This phosphine was measured for elementary analysis, infrared absorption spectrum and $^1H$-NMR spectrum. The results are shown in Table 1, FIG. 2 and FIG. 4, respectively.

TABLE 1

| | Elementary analysis | | | | | |
|---|---|---|---|---|---|---|
| | Calculated (%) | | | Found (%) | | |
| | C | H | O | C | H | O |
| Example 1 | 74.29 | 7.62 | 11.00 | 73.93 | 7.78 | 11.23 |
| Example 7 | 75.29 | 8.21 | 10.03 | 75.07 | 8.33 | 10.23 |

[Polymerization of conjugated diene]

Polymerization was conducted by repeating the same procedure as in Example 1, except that the tris(3,5-dimethyl-4-ethoxyphenyl)phosphine obtained above was substituted for the tris(3,5-dimethyl-4-methoxyphenyl)phosphine used in Example 1. The results are shown in Table 2.

EXAMPLE 8

[Preparation of nickel complex]

A 50-ml flask equipped with a reflux condenser and a dropping funnel was purged with nitrogen. Therein were placed 0.873 g (2.0 mmols) of tris(3,5-dimethyl-4methoxyphenyl)phosphine and 10 ml of diethyl ether. To the mixture was dropwise added 0.171 g (1.0 mmol) of nickel tetracarbonyl under reflux. After the completion of the dropwise addition, the reaction mixture was heated under reflux for a further 30 minutes and then cooled. The precipitated crystals were collected by filtration and suction-dried to obtain a niclel complex represented by the formula:

$$Ni(CO)_2[P(\text{―}C_6H_2(CH_3)_2\text{―}OCH_3)_3]_2]$$

[Oligomerization]

The whole of the nickel complex prepared above was placed in an autoclave purged with nitrogen. Thereto were added 100 ml of deoxygenated toluene and 60 g of butadiene, and the resulting mixture was stirred at 90° C. for 24 hours. The reaction mixture was cooled and analyzed by gas chromatography to find that the starting butadiene was consumed completely and that 4-vinylcyclohexene, (Z,Z)-1,5-cyclooctadiene and (E,E)-1,5,9-dodecatriene were produced in yields of 21%, 68% and 11%, respectively.

TABLE 2

| | Organic phosphorus compound or its cobalt complex compound | Amount of cobalt (mmol) | Polymerization temp. (°C.) | Yield of polymer (g) | Vinyl content (%) | Crystallinity (%) | [η] (dl/g) | Al/Co (molar ratio) | H₂O/Al (molar ratio) |
|---|---|---|---|---|---|---|---|---|---|
| Example 1 | Tris(3,5-dimethyl-4-methoxyphenyl)phosphine | 0.072 | −5 | 27.3 | 98 | 38 | 1.38 | 11.1 | 0.5 |
| Example 2 | Tris(3,5-dimethyl-4-methoxyphenyl)phosphine | 0.072 | 0 | 30.1 | 96 | 36 | 1.45 | 11.1 | 0.5 |
| Example 3 | Tris(3,5-dimethyl-4-methoxyphenyl)phosphine | 0.072 | 10 | 34.3 | 95 | 33 | 1.15 | 11.1 | 0.5 |
| Example 4 | Cobalt bromide-tris(3,5-dimethyl-4-methoxyphenyl)-phosphine complex | 0.072 | −5 | 26.5 | 98 | 38 | 1.45 | 11.1 | 0.5 |
| Example 5 | Tris(3,5-dimethyl-4-dimethylaminophenyl)-phosphine | 0.072 | −5 | 25.9 | 98 | 38 | 1.27 | 11.1 | 0.5 |
| Example 6 | Tris(3,5-dimethyl-4-methoxyphenyl)phosphine | 0.0615 | −5 | 31.0 | 98 | 38 | 1.68 | 13 | 0.5 |
| Example 7 | Tris(3,5-dimethyl-4-ethoxyphenyl)phosphine | 0.072 | −5 | 28.1 | 98 | 38 | 1.25 | 11.1 | 0.5 |
| Comparative Example 1 | Tris(3,5-xylyl)phosphine | 0.072 | −5 | 15.5 | 97 | 37 | 1.03 | 11.1 | 0.5 |
| Comparative Example 2 | Triphenylphosphine | 0.072 | −5 | 25.2 | 92 | 31 | 0.95 | 11.1 | 0.5 |
| Comparative Example 3 | Tris(2,6-dimethoxyphenyl)-phosphine | 0.072 | −5 | 0 | — | — | — | 11.1 | 0.5 |
| Comparative Example 4 | Cobalt bromide-bis-(triphenylphosphine) complex | 0.072 | −5 | 27.1 | 92 | 31 | 1.05 | 11.1 | 0.5 |
| Comparative Example 5 | Tris(3,5-dimethyl-4-methoxyphenyl)phosphine | 0.072 | −5 | 0 | — | — | — | 11.1 | 2 |

What is claimed is:

1. A process for producing a conjugated diene polymer, which comprises polymerizing butadiene-1,3 in a hydrocarbon or halogenated hydrocarbon solvent in the presence of
   (A) a cobalt compound selected from the group consisting of cobalt(II)-triphenylphosphine complex, cobalt(II) acetylacetonate, cobalt octenoate, cobalt naphthenate, cobalt(II) chloride, cobalt(II) bromide, cobalt(II) iodide, pyridine complexes of these cobalt halides and cobalt ethylxanthogenate,
   (B) an organic phosphorous compound represented by the formula:

wherein R¹ and R² are independently hydrogen atoms, alkyl groups or aryl groups, provided that at least one of R¹ and R² is an alkyl group, and three X's, which may be the same or different, are independently selected from the group consisting of a methoxy group, an ethoxy group, a propoxy group, a butoxy group, a phenoxy group, a hydroxyl group, a dimethylamino group, a diethylamino group, a dipropylamino group, a dibutylamino group, a methylamino group, an ethylamino group and an amino group,
   (C) an organoaluminum compound selected from the group consisting of triethylaluminum, tripropylaluminum, triisopropylaluminium, tributylaluminum, triisobutylaluminum, trihexylaluminum, triphenylaluminum, diethylaluminum monochloride, dipropylaluminum monochloride and diisobutylaluminum monochloride, and
   (D) 0.25–1.5 mole, per mole of the organoaluminum compound (C), of water.

2. The process according to claim 1, wherein the three electron-donating groups (X's) of the organic phosphorus compound (B) are independently selected from methoxy group and ethoxy group.

3. The process according to claim 1, wherein R¹ and R² of the organic phosphorus compound (B) are independently alkyl groups having 1–4 carbon atoms.

4. The process according to claim 3, wherein the alkyl group is a methyl group.

5. The process according to claim 1, wherein the organoaluminum compound (C) is used in a proportion of 1–1,000 mols per mol of the cobalt compound (A).

6. The process according to claim 5, wherein the proportion is 5–100 mols.

7. The process according to claim 1, wherein the water (D) is used in a proportion is 0.5–1 mol per mol of the organoaluminum compound (C).

8. The process according to claim 1, wherein the organic phosphorus compound (B) is used in a proportion of 0.5 mol or more per mol of the cobalt compound (A).

9. The process according to claim 8, wherein the proportion is 0.5–10 mols.

10. The process according to claim 8, wherein the proportion is 1–5 mols.

11. The process according to claim 1, wherein the cobalt compound (A) is used in a proportion of 0.01–1 mmol per mol of the butadiene 1,3.

12. The process according to claim 11, wherein the proportion is 0.01–0.5 mmol.

13. The process according to claim 1, wherein the conjugated diene polymer obtained has a crystallinity of 10–50%.

14. The process according to claim 1, wherein the conjugated diene polymer obtained has a vinyl content of 90% or more.

15. The process according to claim 1, wherein the conjugated diene polymer obtained has a vinyl content of 93% or more.

* * * * *